US005874313A

United States Patent [19]
Ahotupa

[11] Patent Number: 5,874,313
[45] Date of Patent: Feb. 23, 1999

[54] METHOD FOR QUANTIFYING OXIDATION PARAMETERS OF LOW DENSITY LIPOPROTEINS AND USE THEREOF

[75] Inventor: Markku Ahotupa, Turku, Finland

[73] Assignee: Oy Aboatech AB, Turku, Finland

[21] Appl. No.: 823,993

[22] Filed: Mar. 25, 1997

[51] Int. Cl.⁶ .......................... G01N 21/76; G01N 33/92
[52] U.S. Cl. .............................. 436/71; 436/172; 436/178
[58] Field of Search .............................. 436/62, 71, 172, 436/177, 178; 422/52

[56] References Cited

PUBLICATIONS

Wieland, H. et al "A simple specific method for precipitation of low density lipoproteins" Journal of Lipid Research, vol. 24 (1983) pp. 904–909.

Lissi, E. et al "Evaluation of total antioxidant potential (TRAP) and total antioxidant reactivity from luminol–enhanced chemiluminescence measurements" Chemical Abstracts, vol. 122 (1995) abstract No. 127879m.

Kujala UM, et al., "Low LDL oxidation in veteran endurance athletes," Scandinavian Journal of Medicine & Science in Sports, 1996.

D.D.M. Wayner, et al., "Quantitative measurement of the total, peroxyl radical–trapping antioxidant capability of human blood plasma by controlled peroxidation," FEBS Letters, 187: 33–37 (1985).

Juha Alanko, et al., "Modulation of Arachidonic Acid Metabolism By Phenols: Relation to Positions of Hydroxyl Groups and Peroxyl Radical Scavenging Properties," Radical Biology & Medicine, vol. 14, 1993.

H.A. Kleinveld, et al. "Improved Measurement of Low–Density–Lipoprotein Susceptibility to Copper–Induced Oxidation: Application of a Short Procedure for Isolating Low–Density Lipoprotein," Clin. Chem. 1992.

Vasankari, et al., "Measurement of serum lipid peroxidation during exercise using three different methods: diene conjugation, thiobarbituric acid reactive material and fluorescent chromolipids" CCA 234 (1995).

*Primary Examiner*—Jeffrey Snay

[57] ABSTRACT

A method for the determination of the oxidizability of low density lipoproteins (LDL) in a serum or plasma sample from a mammal, which method comprises isolating the LDL from the serum or plasma sample for the preparation of a LDL fraction, separating the lipids from the LDL fraction to obtain a lipid fraction therefrom, determining the baseline level of conjugated dienes (BDC) in the lipid fraction.

11 Claims, 8 Drawing Sheets

5,874,313

METHOD FOR QUANTIFYING OXIDATION PARAMETERS OF LOW DENSITY LIPOPROTEINS AND USE THEREOF

FIELD OF THE INVENTION

The present invention relates to methods for measuring oxidation parameters of low density lipoproteins (LDL), which methods are rapid, simple to perform, and valid for the determination of LDL oxidation products and LDL antioxidant potential. These methods provide specific means for assessing the oxidative stress in the body of an individual in general and, in particular, for assessing or screening the risk for, and for the diagnosis, management and research of atherosclerosis and coronary heart disease.

BACKGROUND OF THE INVENTION

Oxidation of low-density lipoprotein plays a key role in processes leading to the development of atherosclerosis. LDL oxidation is accompanied by alterations in its biological properties resulting in, for example, accelerated uptake through scavenger receptors in macrophages, altered chemotactic behavior of monocytes, and monocyte-derived macrophages, endothelial cell damage, and increased amounts of mediators of cell proliferation and platelet aggregation (refs. 1–4). All these effects may contribute to the development of atherosclerotic lesions. Therefore, determination of the LDL oxidation related parameters, namely LDL oxidation products, and antioxidant potential, gives more specific information on atherosclerosis-related biochemical phenomena than the commonly used measurements, of which the most common are the measurement of serum cholesterol, LDL and other lipoproteins and the apolipoproteins.

Most of The data on LDL oxidation come from studies where oxidation of LDL fractions, isolated by conventional ultracentrifugation methods, has been monitored by the appearance of conjugated dienes or thiobarbituric acid reactants arising during oxidation of isolated LDL in vitro (5). Thus far, when LDL oxidation has been investigated in humans in vivo, analyses of LDL oxidation products have been based on antibodies raised against in vitro oxidatively damaged LDL (5). The existing methodology is complex and time-consuming and, in addition, the specificity of the immunological analyses can be questioned (3). Therefore, there is still need for single rapid and specific measurement of LDL oxidation that could become part of the laboratory repertoire in the diagnosis and management of atherosclerosis (5).

The immunological methods developed for direct measurement of oxidized LDL may not be specific, as, in addition to oxidized LDL, antibodies seem to recognize also other epitopes (6) and have given contradictory results as well (3). The poor applicability of immunological methods may be a reflection of the chemistry of LDL oxidation: LDL oxidation can be initiated in various different polyunsaturated fatty acids, and each of these can give rise to a number of different kinds of oxidation products. Due to the multiplicity of oxidation products, development and use of immunological methods is likely to remain problematic also in the future.

The existing methods for measuring the antioxidant potential of LDL are complex and time consuming, and for example only a limited number of analyses can be performed within one working week: LDL is first isolated by ultracentrifugation, whereafter the samples still have to be dialyzed. Another disadvantage is the unprecise recording of results, where changes of the various reaction phases are not always easily detected.

We have developed, for the analysis of LDL oxidation parameters, namely LDL oxidation products and LDL antioxidant potential, methods which are rapid and simple to perform, and can therefore be used for large-scale clinical studies. The validity and clinical applicability of these analytical procedures is clearly indicated by several studies.

SUMMARY OF THE INVENTION

The objects of the present invention are fulfilled by providing a method for the determination of the oxidizability of low density lipoproteins (LDL) in a serum or plasma sample from a mammal, which method comprises isolating the LDL from the serum or plasma sample for the preparation of a LDL fraction, separating the lipids from the LDL fraction to obtain a lipid fraction therefrom, determining the baseline level of conjugated dienes (BDC) in the lipid fraction.

In a preferred embodiment of this invention, the method additionally includes the following steps:

isolating the LDL fraction from the sample by precipitation, preferably by buffered heparin, drying the extracted lipid fraction, redissolving the dried lipid fraction in an organic solvent, analyzing the dissolved lipid fraction spectrophotometrically.

According to a further embodiment, the invention concerns a method for the determination of the antioxidant potential of LDL in a serum or plasma sample from a mammal, comprising the steps of:

isolating the LDL from the serum or plasma sample for the preparation of a LDL fraction, subjecting the LDL fraction to a 2,2'-azobis(2-amidinopropane)HCl (ABAP) induced peroxidation reaction and determining the total peroxyl radical trapping antioxidant potential (LDL-TRAP) of the sample, preferably by using chemiluminescence.

It is a further object of this invention to provide a method of screening the risk for, the diagnosis, management and research of atherosclerosis and coronary heart disease in a mammal, comprising the steps of obtaining a serum or plasma sample from the mammal, isolating the LDL from the serum or plasma sample for the preparation of a LDL fraction, separating the lipids from the LDL fraction to obtain a lipid fraction therefrom, determining the baseline level of conjugated dienes (LDL-BDC) in the lipid fraction, comparing the values obtained with reference ranges for LDL-BDC determined for a group of healthy individuals.

It is still a further object of this invention to provide a kit for use in the screening of the risk for, the diagnosis, management and research of atherosclerosis and coronary heart disease comprising means for isolating LDL from a serum or plasma sample for the preparation of a LDL fraction, and means for separating the lipids from the LDL fraction to obtain a lipid fraction.

Further areas of applicability of the present invention will be apparent from the detailed description given hereinafter.

The LDL-BDC method according to the present invention is thus based on the determination of the "diene conjugation", by which is meant the rearrangement of the double bonds in polyunsaturated fatty acids, which is an early event in the process of lipid peroxidation (7). This rearrangement is known to cause a specific change in UV-absorption of the fatty acid molecule. This is advantageous in two important ways: (i) diene conjugation occurs only during peroxidation of polyunsaturated fatty acids; (ii) diene conjugation is a common step in peroxidation of all polyunsaturated fatty acid molecules. In experimental in vitro studies on LDL oxidizability, the diene conjugation is regarded as the most reliable index, and is widely used in this context (5). The LDL-BDC method according to the present invention, however, is the first method used for the direct measurement of LDL diene conjugation in vivo, without oxidation of the serum or plasma sample.

The method used according to the present invention for measuring the antioxidant potential (LDL-TRAP) is, in contrast to the previously known methods, rapid (isolation of LDL and the measurements are done within the same day) and accurate (the sensitive chemiluminescence-based detection allows exact determination of the lag time period).

BRIEF DESCRIPTION OF THE DRAWINGS

The invention as well as other objects, features and advantages thereof will be understood more clearly and fully from the following detailed description, with reference to the accompanying drawings, in which.

DETAILED DESCRIPTION OF THE INVENTION

Figure 1:
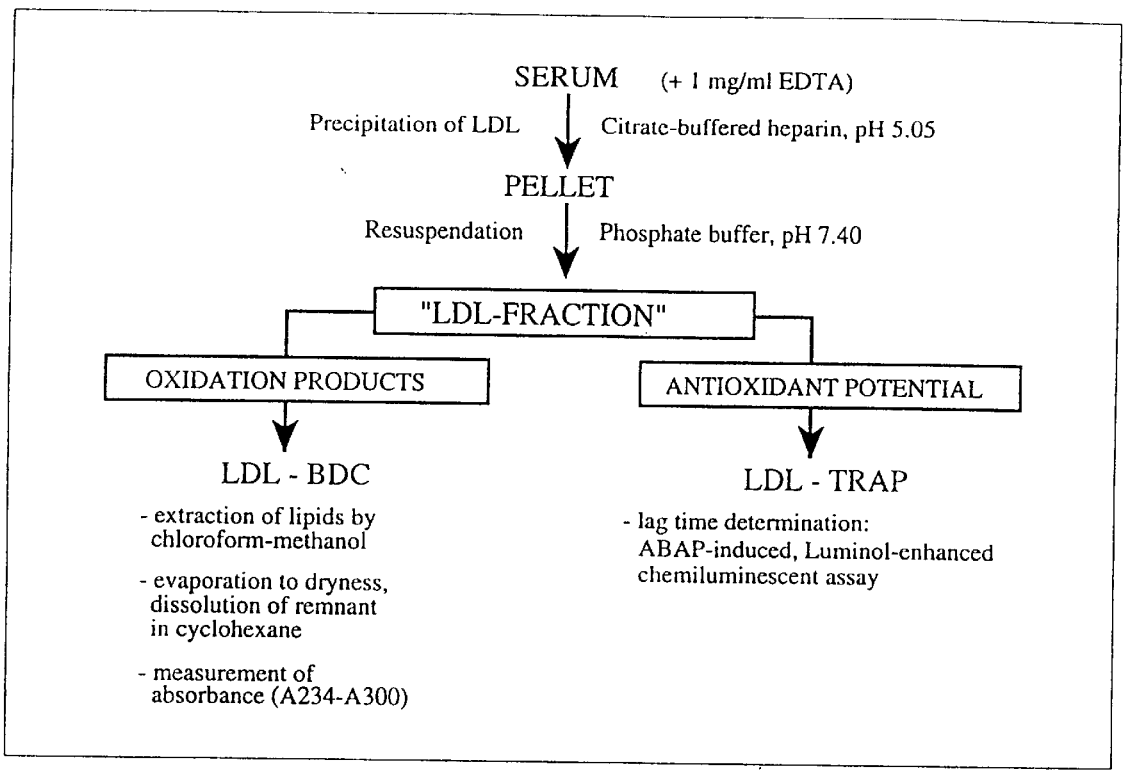
FIG. 1 is an overview of the preferred methods for determination of LDL oxidation products (LDL-BDC) and antioxidant potential (LDL-TRAP) in the serum.

According to a preferred embodiment of the present invention, LDL is isolated by a fast precipitation method and the assay for LDL oxidation products (LDL-BDC) is based on spectrophotometric determination of baseline levels of conjugated dienes (BDC) in lipids extracted from LDL.

For performing the LDL-BDC and LDL-TRAP assays, 0.5 ml of serum or plasma is generally sufficient. In addition to fresh serum or plasma, frozen samples (studied for a period of 6 months at −70° C.), too, can be used for the assays after thawing at room temperature.

According to a preferred embodiment of the invention, serum LDL is preferably isolated by precipitation with buffered heparin (8) after allowing the serum samples and precipitation reagents to equilibrate to room temperature. The serum sample, the volume of which can suitably be 0.2 to 1.7 ml, preferably 1 ml, is added to 1 to 7 ml, preferably 7 ml, of the precipitation buffer. The insoluble lipoproteins are then sedimented by centrifugation and the pellet is resuspended in a sodium phosphate buffer, pH 7.4 (0.5 to 1 ml). The LDL sample or fraction so obtained can be used as such for the quantification of oxidation products and antioxidant potential.

For measuring the LDL-BDC, lipids are extracted from LDL samples with a suitable organic solvent or solvent system, such as a chlorinated organic solvent, e.g. a chlorinated alkane, with a lower aliphatic alcohol. The sample size is usually 0.05 to 0.50 ml, preferably 0.10 ml. The chlorinated organic alkane can be e.g. chloroform or methylene chloride. Preferably, the organic solvent is chloroform and the lower aliphatic alcohol is methanol. The chloroform:methanol ratio may range from 2:1 to 4:1, and is preferably 3:1. The volume depends on sample size and ranges from 3 to 20 ml.

The mixture is then dried under argon or nitrogen, preferably under nitrogen, then redissolved in an organic solvent, which is "inert" in the subsequent spectrophotometrical analysis, such as an inert aliphatic hydrocarbon, e.g. an alkane or a cycloalkane, preferably a cyclohexane, and analyzed spectrophotometrically at 234 and 300 nm. Absorbance at 300 nm is subtracted from that at 234 nm. The Δ absorbance may be converted to molar units using the molar extinction coefficient $2.95 \times 10^4 M^{-1} cm^{-1}$. The results can be expressed μmol/l serum to give an estimation of the actual level of circulating oxidized LDL.

The assay for the antioxidant potential (total peroxyl radical trapping antioxidant potential, TRAP) of LDL (LDL-TRAP) is based on a luminometric determination of the ability of LDL to resist peroxyl radical-induced lipid peroxidation.

For such a measurement, sodium phosphate incubation buffer, pH 7.4, and the LDL sample (buffer 0.45 ml, sample size 0.05 to 0.20 ml, preferably 0.10 ml) are mixed in a cuvette and the assay is initiated by addition of ABAP. Chemiluminescence is measured at 37° C. until a peak value for each sample is detected. Determination of the peroxyl radical trapping capacity is based on lag time determination which is defined by the half-peak time point, and trolox is used as a standard radical scavenger. To get an estimation of the relative antioxidant power of given LDL preparations, the results can be expressed in relation to the cholesterol concentration of the preparations.

An overview of the preferred measurements of LDL-BDC and LDL-TRAP is indicated in the FIG. 1.

According to the present invention it has been clearly indicated that BDC and TRAP can be readily measured in LDL by the described methods.

Measurement of LDL-BDC can be done in a similar way in heparin precipitated LDL as in LDL isolated by ultracentrifugation, the heparin precipitation method, however, offering several advantages over ultracentrifugation especially from a laboratory technical point of view.

The results obtained by the LDL-BDC method are well in accordance with those obtained by the immunological method.

High LDL-BDC values are indicative of increased risk for atherosclerosis, as suggested by the positive correlation with the thickness of arterial wall, and also indirectly by the results from studies where the LDL-BDC levels were found to alter parallelly to various known factors increasing the risk (diabetes, obesity etc.) for, or protecting (physically active life-style etc.) from atherosclerosis.

The LDL-TRAP value is indicative of the antioxidant potential of LDL, as indicated by the negative correlation with LDL-BDC, and also by the antioxidant intervention studies.

The results obtained in the LDL-BDC and LDL-TRAP methods can thus be used as indicators in the screening of the risk for, the diagnosis and management, including follow-up treatment, of atherosclerosis and coronary heart disease. In addition, these methods will be useful in a broad scale of studies and research on the etiology (e.g. the role of genetic, dietary, environmental or life style-dependent factors), prevention (e.g. the effect of dietary factors, physical activity, drugs) and management of atherosclerosis and coronary heart disease.

The reference ranges for LDL-BDC and LDL-TRAP are obtained laboratory specifically by measuring the LDL-BDC and LDL-TRAP values of a large number (e.g. 200–300) healthy human adults and calculating the corresponding mean values (with standard deviations). A high LDL-BDC value (close to the upper limit of the LDL-BDC reference range or over it), optionally in combination with a low LDL-TRAP value (close to the lower limit of the LDL-TRAP reference range or below it), is indicative of an increased risk for atherosclerosis and/or coronary heart disease. The reference ranges measured by us for healthy human individuals are LDL-BDC appr. 15–60 $\mu$mol/l serum and LDL-TRAP appr. 12–38 $\mu$mol/mmol LDL-cholesterol.

Due to the fact that the LDL-TRAP gives a faster response as a result of treatment and/or changes in life-style habits (diet, exercise), this value is especially advantageous for use as an easy and rapid means for the treatment follow-up of atherosclerosis and coronary heart disease.

The following Examples will further illustrate the present invention, which by no means limit the invention.

EXAMPLE

Precipitation of LDL

Serum LDL is isolated by precipitation with buffered heparin. The precipitation buffer is 0.064M trisodium citrate adjusted to pH 5.05 with 5N HCl, containing 50,000 IU/l heparin (5,000 IU/ml heparin was obtained either from Loevus Kemiska Fabrik, Ballerup, Denmark, or from Leiras Ltd, Turku, Finland). Before precipitation of LDL, serum samples (to which 1 mg/ml of EDTA is added) and precipitation reagents are allowed to equilibrate to room temperature. One milliliter of the serum sample is added to 7 ml of the precipitation buffer. After mixing with a Vortex mixer, the suspension is allowed to stand for 10 min at room temperature. The insoluble lipoproteins are then sedimented by centrifugation at 1,000 g for 10 min. The pellet is resuspended in 1 ml of 0.1M sodium phosphate buffer, pH 7.4, containing 0.9% of NaCl. This LDL sample can be used as such for the analysis of oxidation products and antioxidant potential.

Determination of the oxidation products of LDL (LDL-BDC)

Lipids are extracted from LDL samples (sample size 0.10 ml) by adding 1 ml of methanol and 3 ml of chloroform (mixing with a Vortex mixer after S the addition of each solvent). Then the mixture is allowed to stand for one hour at room temperature in the dark, after which 2 ml of water is added, the mixture is mixed with a Vortex mixer and then centrifuged at 2,000 g for 10 min at +8° C. The lower phase is evaporated to dryness under nitrogen, resuspended in 1 ml of cyclohexane and analyzed spectrophotometrically (Perkin-Elmer Lambda 2 spectrofotometer) at 234 and 300 nm.

Determination of the antioxidant potential of LDL (LDL-TRAP)

Figure 2:
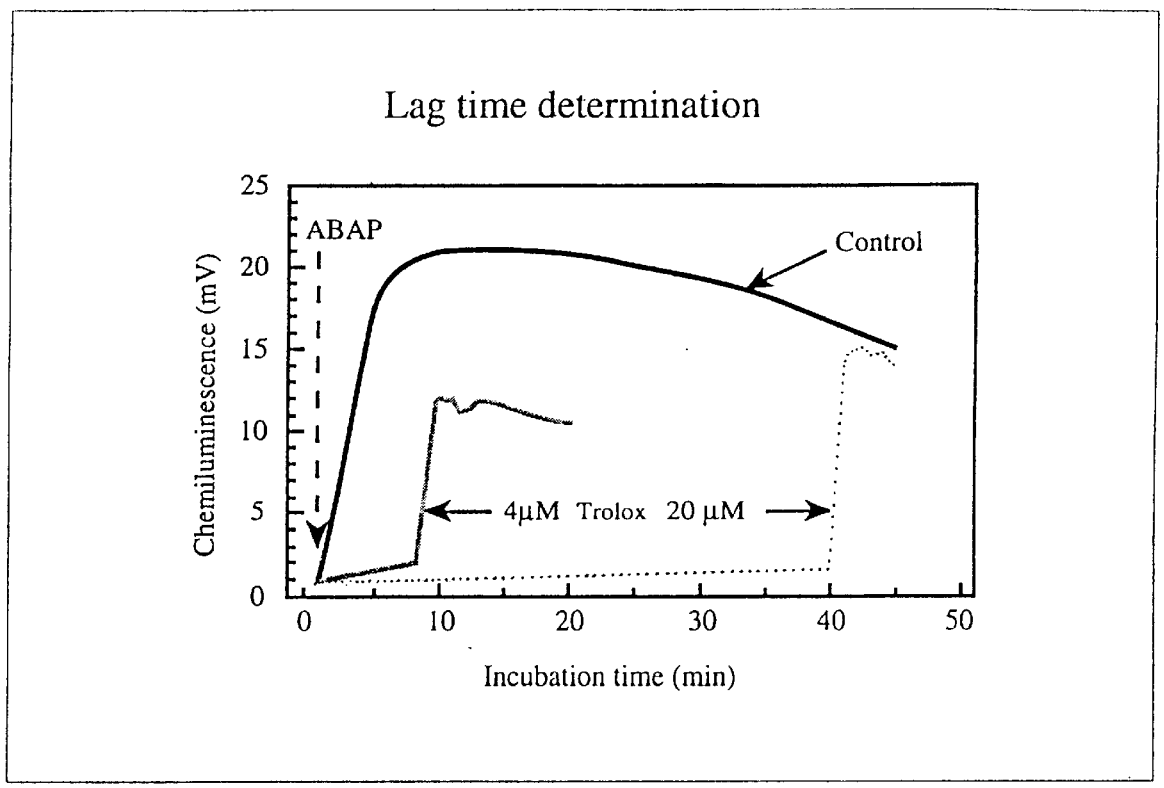
FIG. 2 is a graph, which shows the chemiluminescence lag time determination assay for LDL antioxidant potential (LDL-TRAP).

0.45 ml of incubation buffer (0.1M sodium phosphate buffer, pH 7.4, containing 0.9% of NaCl, 0.02 ml of 120 mM linoleic acid, 0.05 ml of luminol [0.5 mg/ml, obtained from Bio-Orbit Ltd., Turku, Finland]) and 0.10 ml of LDL sample are mixed in the cuvette and the assay is initiated with 0.05 ml of ABAP (83 mg/ml, obtained from Polysciences Inc., Warrington, Pa., USA). Chemiluminescence measurements are performed with Bio-Orbit 1251 Luminometer. Chemiluminescence in duplicate cuvettes is measured at 37° C. until a peak value for each sample is detected (see FIG. 2).

VALIDITY OF THE METHODS

Heparin precipitation is a specific and reproducible means for isolation of LDL from serum samples. In this LDL preparation, LDL-BDC and LDL-TRAP can be measured and the assays show good reproducibility and linearity, as can be seen from the results shown below.

To assess the reliability of the heparin-citrate precipitation method, the linearity with respect to sample size and reproducibility of the method were investigated. The reproducibility of LDL precipitation was tested by repeating the procedure 20 times from a pool of serum, and analyzing the apolipoprotein B (apoB) contents in precipitated LDL. Reagent kits for apolipoprotein B was obtained from Orion Diagnostica, Espoo, Finland. The coefficient of variation (CV) for the within-assay precision was 6.7% for apoB.

Figure 3:
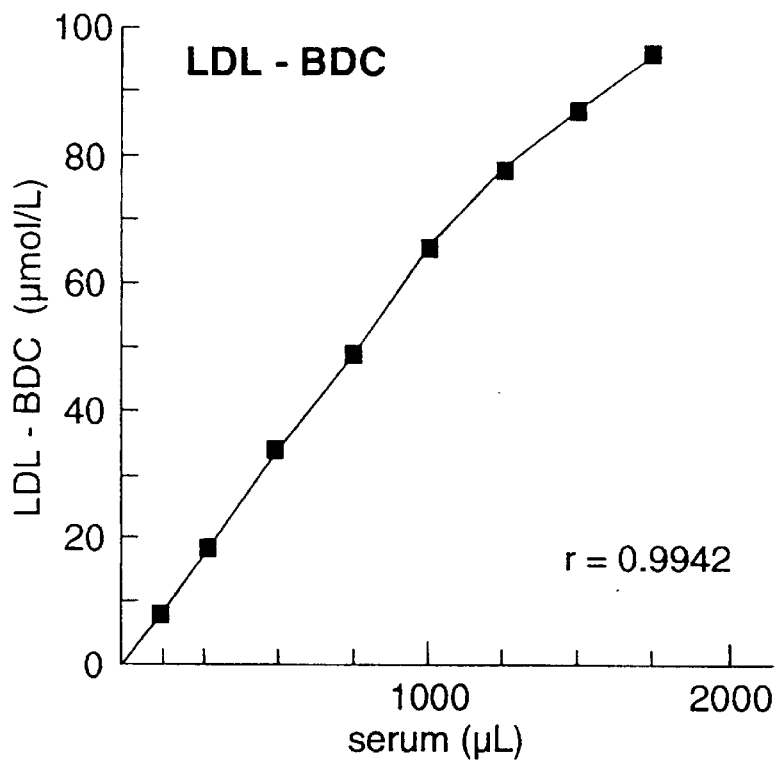
FIGS. 3A and 3B show the linearity of A. LDL-BDC and B. LDL-TRAP with respect to sample size and reproducibility of the heparin-citrate precipitation method.
Figure 3:
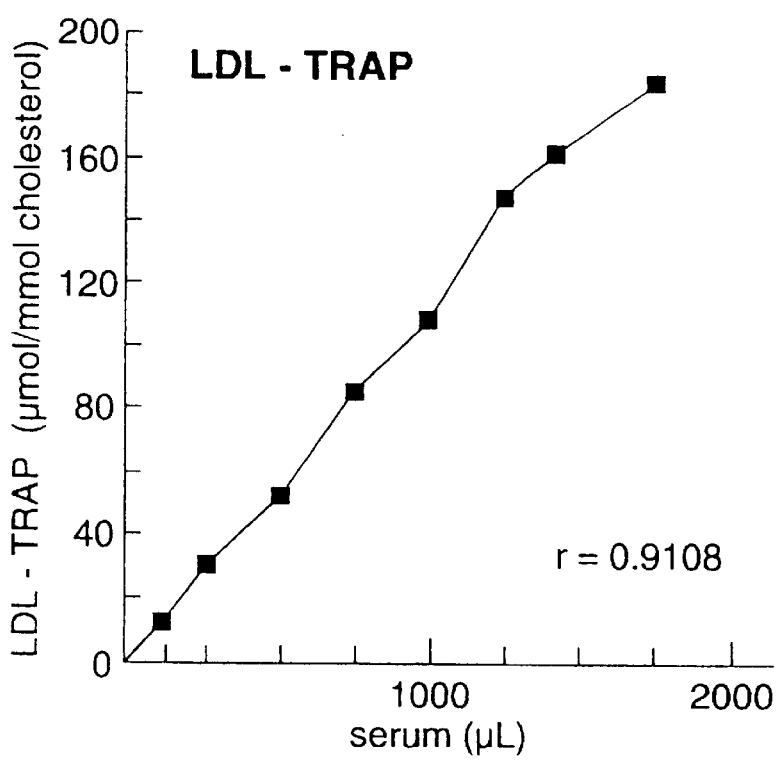

The LDL-BDC was detectable in LDL precipitated from 100 $\mu$l of serum, and the amount of LDL-BDC was directly proportional to the amount of serum taken for precipitation (FIG. 3A). Similarly, LDL-TRAP increased linearly with increasing amounts of serum and was reliably detectable in LDL precipitated from 260 $\mu$l of serum (FIG. 3B). For LDL-BDC, the CV for within-assay precision was 4.4%, and CV for the between-assay precision over a period of 3 months was 4.5%. With the LDL-TRAP, the CV for the within-assay precision was 8.1, and CV for the between-assay precision over a period of 3 months was 8.7%.

Freezing of the serum (studied for a period of 6 months at −70° C.) did not affect LDL-BDC or LDL-TRAP levels.

The relationship between LDL-BDC and LDL-TRAP and the corresponding measurements in serum, serum lipids, and antioxidants (α-tocopherol, ubiquinol-10), were measured in volunteers (n=31) and the interdependence of the parameters was estimated by correlation analysis. A reagent kit for cholesterol (CHOD-PAP method) was obtained from Boehringer Mannheim, Mannheim, Germany, and the serum concentrations of α-tocopherol (9) and ubiquinol-10 (10) were analyzed by standard HPLC procedures with UV-detection. There was a negative correlation between LDL-BDC and LDL-TRAP (Table 1). LDL-BDC correlated positively with serum diene conjugation, LDL cholesterol, and triglycerides, but no correlation was found to exist between the antioxidant levels and LDL-BDC. LDL-TRAP correlated positively with the serum TRAP value and negatively with serum LDL and cholesterol. Again, no correlation existed between the measured antioxidants and the LDL-TRAP.

The fact that the LDL-BDC and LDL-TRAP values are negatively correlated, further strengthens the validity and credibility of these methods. BDC values measured in heparin precipitated LDL are not different from those measured in LDL isolated by the conventional ultracentrifugation method, as shown by detailed comparison studies (Table 2). For preparative ultracentrifugation we used either a Sorvall OTD-65 ultracentrifuge with fixed-angle rotors or a Kontron TGA-65 ultracentrifuge with swing-out rotors (11, 12). The LDL-TRAP, however, was in this comparison lower in LDL isolated by precipitation. Since no dialysis was performed for LDL after ultracentrifugation, the apparently different TRAP values in LDL fractions isolated by the different methods are likely explained by interfering peroxyl radical trapping components, such as ascorbate, glutathione and urate, present in LDL isolated by ultracentrifugation.

Of the direct methods currently available for estimation of LDL oxidation products, the preferred one has been the immunological method, based on the use of auto-antibodies to epitopes on oxidized LDL (5). When analyzed in the same samples from healthy volunteers (men, age 21–44 years, N=29), this immunological assay shows a good correlation with the LDL-BDC assay (FIG. 4).

Figure 4:
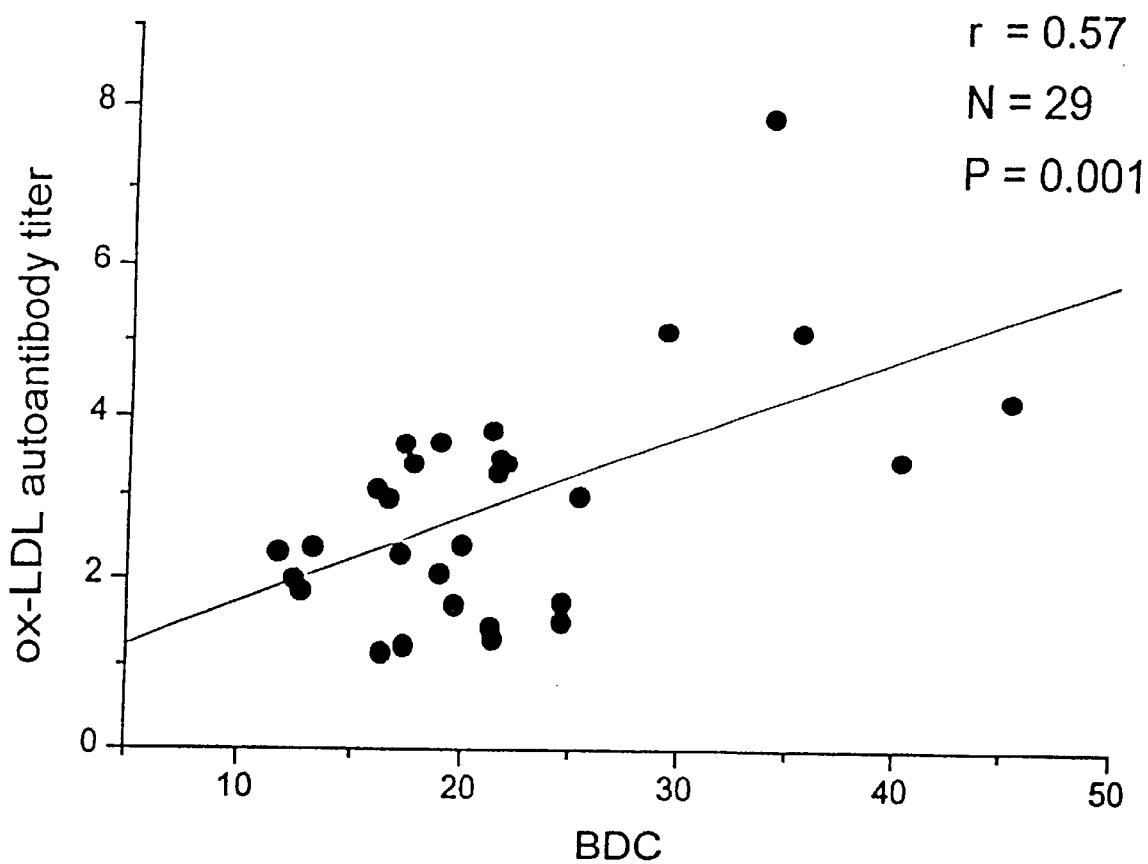
FIG. 4 is a graph, which shows the correlation of LDL-BDC with oxidized LDL measured with the (conventional) immunological autoantibody method.

For obtaining the results in FIG. 4, autoantibody titers of anti-oxidized LDL were measured by enzyme-linked immunosorbent assay method using 96-well polystyrene microtitration plates (Nunc, Immunoplate, Roskilde, Denmark). Antigens for this assay included native LDL, protected against oxidation by 0.27 mM edetic acid and butylated hydroxytoluene (BHT) in phosphate buffered saline (PBS, 10 mM sodium phosphate, pH 7.2), and ox-LDL (obtained after 18 h oxidation with 2 $\mu$M $CuSO_4$, and prepared from the pooled plasma of ten donors (12). The wells were incubated (coated) with 50 $\mu$L of native and ox-LDL antigen (5 $\mu$g/ml) (protected from oxidation as noted above) in PBS for 16 h at 4° C. After removal of the unbound antigen and washing of the wells (three times with PBS, 0.5% Tween 20, and three times with distilled water, using microtiter plate washer BioRad Model 1550), the remaining non-specific binding sites were saturated using 2% bovine serum albumin in PBS. The wells were washed, and 50 $\mu$L of serum sample (diluted to 1:20 and 1:50) were added to wells coated with native LDL and ox-LDL, and incubated over night at 4° C. After incubation, the wells were aspirated and washed, before an appropriate IgG-peroxidase conjugated rabbit antihuman monoclonal antibody (Organon, USA, no. 55220 Cappel, diluted to 1:4,000 in 0.27 mM PBS, 20 $\mu$M edetic acid, 1 % BHT, bovine serum albumin-0.05% Tween) was added to each well (0.5 ml). After incubation (for 4 h at 4° C.), the unbound material from the wells were aspirated and wells washed. After this, 0.5 ml of freshly prepared substrate (0.4 mg/ml o-phenylenediamine, Sigma, and 0.045% $H_2O_2$ in 100 mM acetate buffer, pH 5.4) was added and incubated for 5 min at room temperature. The enzyme reaction was terminated by addition of 0.5 ml of 2M $H_2SO_4$. The optical density was then measured spectrophotometrically at 492 nm with a special microplate reader (Multiscan MCC/340, Labsystems GmbH, Munich, Germany). To calculate the antibody titer, we used the ratio of the corresponding spectrophotometric reading of anti-oxidized LDL and the anti-native LDL wells from the same serum sample. Using this approach, the spectrophotometric readings of anti-native LDL wells represent the corresponding blanks of anti-oxidized LDL wells and reduce the possible detection of false positive values.

CLINICAL APPLICABILITY OF THE METHODS

Clinical applicability of LDL-BDC and LDL-TRAP has been tested among patients and volunteers with known disease- or life style dependent factors increasing or decreasing the risk of atherosclerosis and coronary heart disease (CHD). In addition, applicability of the LDL-TRAP method has been tested by antioxidant intervention studies.

Progression of atherosclerosis is commonly estimated by measuring the thickness of the arterial walls by ultrasound techniques. The ultrasound technique was used for measurement of the (intima-media) thickness of arteria carotis among 33 men (age 21–46 years), and LDL oxidation products from these subjects were determined by the LDL-BDC method. A positive correlation (r=0.43; p=0.012) was found to exist between the LDL-BDC values and thickness of the arteria carotis.

Diabetes

Non-insulin-dependent diabetes is known to be associated with increased risk for atherosclerosis (13). Samples were collected from patients at the Department of Internal Medicine, Turku University Hospital, Finland. The material includes patients from both sexes, ages 16–88 years. No separation was made with respect to the type of diabetes mellitus and, at times of the sample collection, patients were receiving treatment for the disease.

Figure 5:
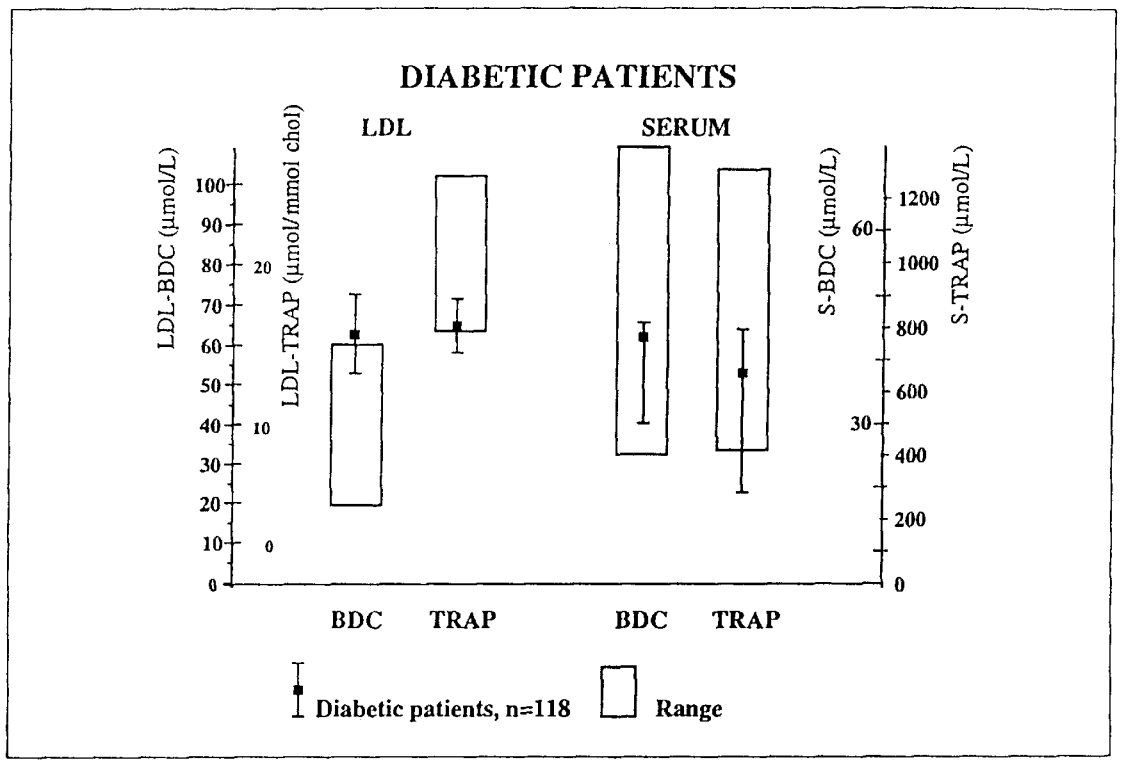
FIG. 5 shows the ranges of BDC and TRAP values of LDL and serum of diabetic patients. The term "range" means normal values based on determinations on healthy volunteers, age 18–70 years, both sexes, N=300.

FIG. 5 shows that LDL-BDC and LDL-TRAP values of patients with diabetes (N=118) clearly differ from those of age-matched healthy controls.

Obesity

Figure 6:
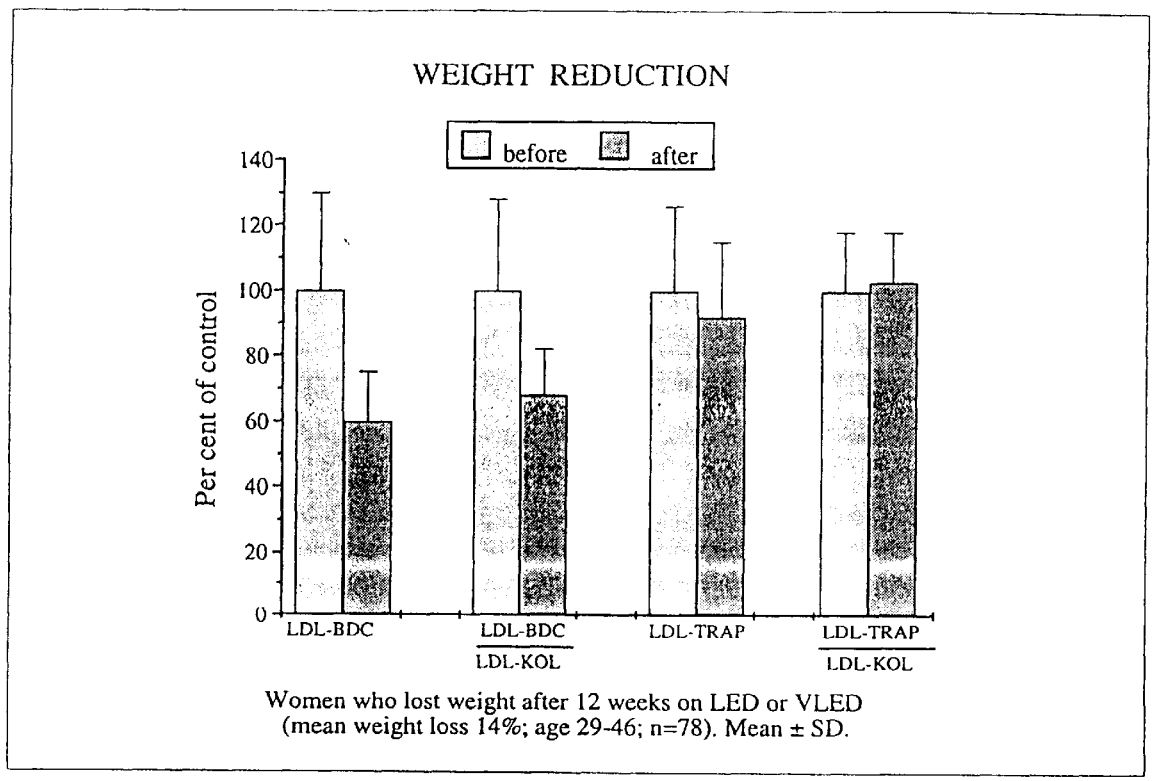
FIG. 6 is a bar graph, which shows the effect of body weight reduction on LDL-BDC and LDL-TRAP values in obese premenopausal women. Weight before onset of diets ranged from 90 to 100 kg. LED, low-energy diet; VLED, very low-energy diet.

Obesity is an independent risk factor for CHD mortality among men and also contributes to the risk of CHD among women (14). When measured in healthy volunteers (men, age 40–49 years, N=31) LDL-BDC was found to correlate positively with the body mass index (r=0.47, p=0.008). Controlled reduction of body weight among obese premenopausal women (N=82, weight before onset of diets ranged from 90 to 100 kg) decreased significantly LDL-BDC levels. Total LDL-BDC decreased by 40% and LDL-BDC/total LDL cholesterol ratio by 32% (FIG. 6).

Physical activity

Figure 7:
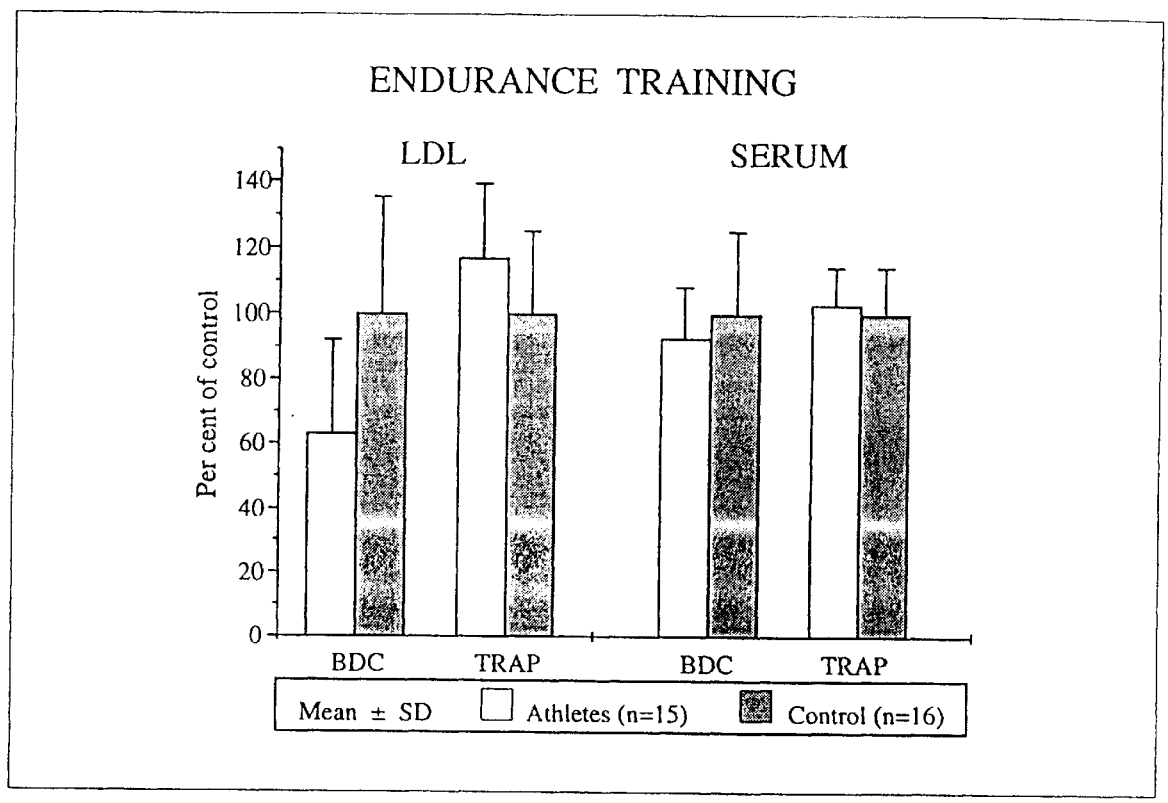
FIG. 7 is a bar graph, which shows the effect of endurance training on BDC and TRAP values in LDL and serum. "Athletes" denote a group of men (age 40–49 years) with a history of several (>1 5) years active endurance training (long-distance running). Control group consisted of men of the same age and weight (body mass index) with no endurance training, but a similar socioeconomic background and dietary and smoking habits.

Physically active life style, in turn, is known to be associated with decreased risk of CHD (15). We found that middle-aged (40–49 years) men (N=31) who are actively participating in endurance training have distinctly lower LDL-BDC values (37%) than age- and weight-matched controls with similar socioeconomic background, and dietary and smoking habits (FIG. 7, see also ref. 16).

Antioxidant intervention

Figure 8:
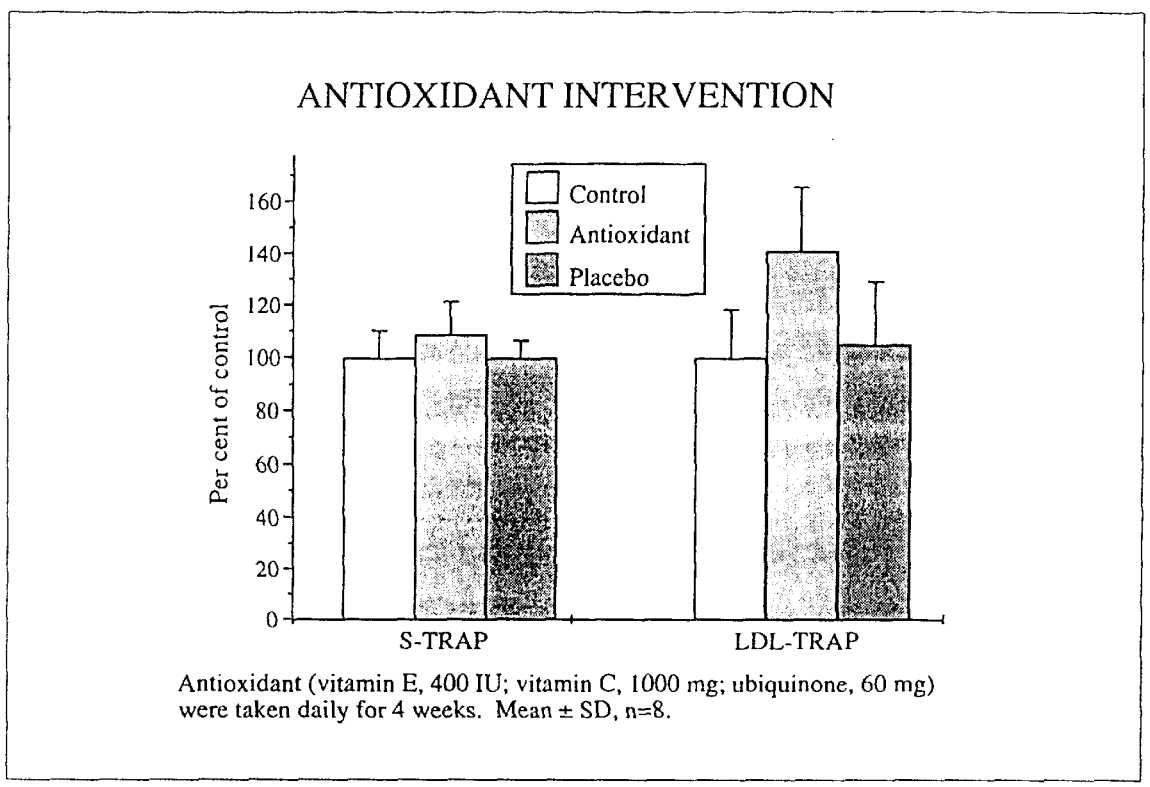
FIG. 8 is a bar graph, which shows the effect of antioxidant intervention on LDL - TRAP and serum TRAP (S-TRAP) values in endurance athletes. Men, age 26–39 years, with 6–21 years history of endurance training. The antioxidant preparations were as follows: vitamin E, Tokovitan®, d-α-tocopheryl acet., Orion. Espoo, Finland; vitamin C, Accorbin®, ascorbic acid, Orion, Espoo, Finland; ubiquinone, Coenzyme Q10®, ubidecarenon., RP Scherer Ltd, Wiltshire, UK. Antioxidants were taken daily for 4 weeks (vitamin E: 400 IU; vitamin C: 1000 mg; ubiquinone: 60 mg).

Two intervention studies have been performed to test the effect of antioxidant preparations (dietary supplements) on LDL-BDC and LDL-TRAP. In the first study (11) vitamin E alone or in combination with vitamin C and β-caroiene was given to volunteers (N=10) a period of one week. In the second (double blind) study (FIG. 8) volunteers received a combination of antioxidants (vitamin E, vitamin C and ubiquinone) for 4 weeks. Serum concentrations of α-tocopherol and ubiquinol-10 were analyzed by standard HPLC procedures with UV-detection. In both of these studies LDL-TRAP values were found to be increased by the antioxidant interventions (by about 40%) while the LDL-BDC levels remained unaffected (for further details, see ref. 17).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

Correlation of LDL oxidation parameters with serum parameters related to LDL oxidation among healthy volunteers (N = 31).

|  | LDL-BDC | LDL-TRAP |
| --- | --- | --- |
| LDL-TRAP | −0.416[1] (p = 0.002) |  |
| Serum BDC | 0.647 (p = 0.0001) | −0.061 (p = 0.756) |
| Serum TRAP | 0.098 (p = 0.600) | 0.546 (p = 0.0015) |
| LDL | 0.676 (p = 0.0001) | −0.565 (p = 0.0009) |
| Serum cholesterol | 0.658 (p = 0.0001) | −0.467 (p = 0.0081) |
| Serum triglycerides | 0.732 (p = 0.0001) | −0.0002 (p = 0.999) |
| Serum α-tocopherol | 0.066 (p = 0.735) | 0.019 (p = 0.922) |
| Serum ubiquinol-10 | 0.357 (p = 0.057) | 0.074 (p = 0.701) |

[1]Correlation coefficient

TABLE 2

Baseline diene conjugation (BDC), thiobarbituric acid reactive material (TBARM) and antioxidant potential (TRAP) in serum and lipoprotein fractions isolated by sequential ultracentrifugation (UC) or heparin precipitation (HEP). Isolation of LDL by ultracentrifugation was performed by the standard procedure as described in ref. 18. LDL isolation by ultracentrifugation and heparin precipitation was repeated 4 times, on separate days and with freshly prepared serum pools. The Roman numerals indicate the different isolation times and serum pools. Results for the various isolation times/serum pools are given as μmol/l, and are mean ± SD from 6 different determinations (from each serum pool, 6 separate LDL samples were isolated). "Total mean" is the mean ± SD of means of the four different serum pools. VLDL, very low-density lipoprotein; HDL, high-density lipoprotein.

|  | Pool | BDC | TBARM | TRAP |
| --- | --- | --- | --- | --- |
| SERUM | I | 71.8 ± 2.7 | 7.40 ± 1.41 | 1071 ± 0 |
|  | II | 68.1 ± 1.1 | 6.60 ± 0.85 | 1193 ± 34 |
|  | III | 57.7 ± 5.9 | 8.20 ± 0.28 | 1071 ± 69 |
|  | IV | 68.3 ± 1.4 |  | 803 ± 34 |
|  | Total mean | 66.5 ± 6.1 | 7.40 ± 0.80 | 1035 ± 165 |
| UC-VLDL | I | 26.4 ± 6.4 | 0.14 ± 0.003 | 206 ± 17 |
|  | II | 20.9 ± 3.3 | 0.20 ± 0.25 | 149 ± 12 |
|  | III | 16.3 ± 2.4 | 0.17 ± 0.12 | 244 ± 35 |
|  | IV | 18.0 ± 3.2 |  | 131 ± 26 |
|  | Total mean | 20.4 ± 4.4 | 0.17 ± 0.03 | 183 ± 52 |
| UC-LDL | I | 25.1 ± 2.8 | 0.43 ± 0.10 | 229 ± 17 |
|  | II | 26.3 ± 2.9 | 0.07 | 200 ± 13 |
|  | III | 23.4 ± 1.1 | 0.18 ± 0.11 | 191 ± 18 |
|  | IV | 30.8 ± 1.8 |  | 192 ± 27 |
|  | Total mean | 26.4 ± 3.2 | 0.23 ± 0.18 | 203 ± 18 |
| UC-HDL | I | 12.6 ± 1.9 | 1.90 ± 0.21 | 288 ± 20 |
|  | II | 20.3 ± 2.3 | 1.27 ± 0.05 | 315 ± 13 |
|  | III | 15.3 ± 2.2 | 1.30 ± 0.14 | 261 ± 26 |
|  | IV | 19.0 ± 1.5 |  | 219 ± 16 |
|  | Total mean | 16.8 ± 3.5 | 1.49 ± 0.36 | 271 ± 41 |
| HEP-LDL | I | 25.1 ± 0.9 | 0.60 ± 0 | 46 ± 3 |

TABLE 2-continued

Baseline diene conjugation (BDC), thiobarbituric acid reactive material (TBARM) and antioxidant potential (TRAP) in serum and lipoprotein fractions isolated by sequential ultracentrifugation (UC) or heparin precipitation (HEP). Isolation of LDL by ultracentrifugation was performed by the standard procedure as described in ref. 18. LDL isolation by ultracentrifugation and heparin precipitation was repeated 4 times, on separate days and with freshly prepared serum pools. The Roman numerals indicate the different isolation times and serum pools. Results for the various isolation times/serum pools are given as μmol/l, and are mean ± SD from 6 different determinations (from each serum pool, 6 separate LDL samples were isolated). "Total mean" is the mean ± SD of means of the four different serum pools. VLDL, very low-density lipoprotein; HDL, high-density lipoprotein.

| Pool | BDC | TBARM | TRAP |
| --- | --- | --- | --- |
| II | 33.3 ± 13.6 | 0.15 ± 0 | 51 ± 3 |
| III | 24.6 ± 0.5 | 0.10 ± 0 | 49 ± 0 |
| IV | 26.7 ± 1.4 |  | 29 ± 0 |
| Total mean | 27.4 ± 4.0 | 0.28 ± 0.28 | 44 ± 10 |

REFERENCES

1 Steinberg D, Parthasarathy S, Carew TE, Khoo, JC, Witztum JL. Beyond cholesterol. Modifications of low-density lipoprotein that increases its atherogenicity. *N Eng J Med* 1989; 320: 915–924.

2 Steinbrecher U P. Zhang H, Lougheed M. Role of oxidatively modified LDL in atherosclerosis. *Free Rad Biol Med* 1990; 9: 155–168.

3 Esterbauer H, Gebicki J, Puhl H, Jurgens G. The role of lipid peroxidation and antioxidants in oxidative modification of LDL. *Free Rad Biol Med* 1992; 13: 341–390.

4 Witztum JL. Role of oxidized low density lipoprotein in atherogenesis. *Br Heart J* 1993; 69 (supplement): S12.

5 Jialal I, Devaraj S. Low-density lipoprotein oxidation, antioxidants, and atherosclerosis: a clinical biochemistry prespective. *Clin Chem* 1996; 42: 498–506.

6 O'Brien KD, Alpers CE, Hokanson JE, Wang S, Chait A. Oxidation-specific epitopes in human coronary atherosclerosis are not limited to oxidized low-density lipoprotein. *Circulation* 1996; 94: 1216–1225.

7 Porter NA. Chemistry of lipid peroxidation. *Methods Enzymol* 1984; 105: 273–282.

8 Wieland H, Seidel D. A simple specific method for precipitation of low density lipoproteins. *J Lipid Res* 1983; 24: 904–909.

9 Milne DB, Bottnen J. Retinol, α-tocopherol, lycopene and β-carotene simultaneously determined in plasma by isocratic liquid chromatography. *Clin Chem* 1986; 32: 874–876.

10 Takada M, lkenoya S, Yuzuhira T, Katayama K. Simultaneous determination of reduced and oxidized ubiquinones. *Methods Enzymol* 1985; 105: 147–155.

11 Ahotupa M, Ruutu M, Mäntylä E. Simple methods of quantifying oxidation products ant antioxidant potential of low density lipoproteins, *Clin Biochem* 1996; 29: 139–144.

12 Heizer T, Yiä-Herttuala S, Luoma J, Kurz S, Munzel T, Just H, Olchewski M, Drexler H. Cigarette smoking potentiates endothelial dysfunction of forearm resistance vessels in patients with hypercholesterolemia. Role of oxidized LDL. *Circulation* 1996; 93: 1346–1353.

13 Pÿörälä K, Laakso M, Uusitupa M. Diabetes and atherosclerosis: an epidemiologic view. *Diabetes Metab Rev* 1987; 3: 463–524.

14 Jousilahti P, Tuomilehto J, Vartiainen E, Pekkanen J, Puska P. Body weight, cardiovascular risk factors and coronary mortality. 15-Year follow-up of middle-aged men and women in Eastern Finland. *Circulation* 1996; 93: 1272–1379.

15 Berlin JA, Colditz GA. Meta-analysis of physical activity in the prevention of coronary heart disease. *Am J Epidemiol* 1990; 132: 612–628.

16 Kujala U, Ahotupa M, Vasankari T, Kaprio J. Tikkanen M. Low LDL oxidation in veteran endurance athletes *Scand J Med Sci Sport* 1996; 6: 303–308.

17 Vasankari TJ, Kujala UM, Vasankari TM, Vuorimaa T, Ahotupa M. Increased serum and LDL antioxidant potential after antioxidant supplementation in endurance athletes. *Am J Clin Nutr* 1997: 65, in press. 18 Schumaker VN, Puppione DL. Sequential flotation ultracentrifugation, *Methods Enzymol* 1986; 128: 155–168.

I claim:

1. Method for the determination of the oxidizability of low density lipoproteins (LDL) in a serum or plasma sample from a mammal, which method comprises isolating the LDL from the serum or plasma sample for the preparation of a LDL fraction, separating the lipids from the LDL fraction to obtain a lipid fraction therefrom, determining the baseline level of conjugated dienes (BDC) in the lipid fraction.

2. The method according to claim 1, wherein the isolation of the LDL is performed by precipitation with buffered heparin.

3. The method according to claim 1, wherein the lipid fraction is separated from the LDL fraction by extraction with an organic solvent, and the method includes the following additional steps:

drying the extracted lipid fraction, redissolving the dried lipid fraction in an organic solvent, analyzing the dissolved lipid fraction spectrophotometrically.

4. The method according to claim 3, wherein the organic extraction solvent is a mixture of a chlorinated alkane and an aliphatic lower alcohol.

5. The method according to claim 3, wherein the organic solvent is a mixture of chloroform and methanol.

6. The method according to claim 3, wherein the solvent used for redissolution is a solvent neutral or inert with respect to the spectrophotometrical method of analysis.

7. The method according to claim 3, wherein the solvent used for redissolution is cyclohexane.

8. The method according to claim 3, wherein the drying of the lipid fraction is performed under nitrogen.

9. The method according to claim 1, further comprising the step of subjecting a LDL fraction to a 2,2'-azobis(2-amidinopropane)HCl (ABAP) induced peroxidation reaction and determining the total peroxyl radical trapping antioxidant potential (LDL-TRAP) of the sample.

10. The method according to claim 9, wherein, in the determination of the LDL-TRAP, chemiluminescence is used.

11. Method of screening the risk for, the diagnosis, management and research of atherosclerosis and coronary heart disease in a mammal, comprising the steps of obtaining a serum or plasma sample from the mammal, isolating the LDL from the serum or plasma sample for the preparation of a LDL fraction, separating the lipids from the LDL fraction to obtain a lipid fraction therefrom, determining the baseline level of conjugated dienes (LDL-BDC) in the lipid fraction, comparing the values obtained with reference ranges for LDL-BDC determined for a group of healthy individuals.

* * * * *